(12) United States Patent
Herrmann et al.

(10) Patent No.: US 8,330,473 B2
(45) Date of Patent: Dec. 11, 2012

(54) APPARATUS AND METHOD FOR THE MEASUREMENT OF MASS AND DENSITY AND/OR FOR THE MEASUREMENT OF THE HUMIDITY OF PORTIONED UNITS

(75) Inventors: Rainer Herrmann, Hamburg (DE); Udo Schlemm, Hamburg (DE); Stefan Zaage, Hannover (DE); Harald Ceslik, Hamburg (DE)

(73) Assignee: TEWS Elektronik GmbH & Co. KG, Hamburg (DE)

( * ) Notice: Subject to any disclaimer, the term of this patent is extended or adjusted under 35 U.S.C. 154(b) by 252 days.

(21) Appl. No.: 12/683,201

(22) Filed: Jan. 6, 2010

(65) Prior Publication Data

US 2010/0176818 A1    Jul. 15, 2010

(30) Foreign Application Priority Data

Jan. 13, 2009 (DE) .................. 10 2009 004 457

(51) Int. Cl.
*G01N 22/04* (2006.01)
(52) U.S. Cl. .......... 324/640; 324/634; 324/643
(58) Field of Classification Search .......... 324/633–643
See application file for complete search history.

(56) References Cited

U.S. PATENT DOCUMENTS

| 6,647,702 B1 | 11/2003 | Kim | |
|---|---|---|---|
| 2004/0124853 A1* | 7/2004 | Moller et al. | 324/633 |
| 2007/0068540 A1 | 3/2007 | Thomas | |

FOREIGN PATENT DOCUMENTS

| CH | 648 733 A5 | 4/1985 |
|---|---|---|
| DE | 101 59 233 A1 | 6/2003 |
| EP | 0 889 321 A1 | 12/1998 |
| EP | 1 316 630 A1 | 3/2002 |
| EP | 1 467 191 A1 | 8/2003 |
| EP | 1 623 925 A1 | 8/2006 |
| EP | 2238847 | 10/2010 |
| EP | 2243384 | 10/2010 |
| EP | 2243385 | 10/2010 |
| GB | 1095848 | 12/1967 |
| WO | 2009099793 A2 | 8/2009 |
| WO | 2010003899 A1 | 1/2010 |

* cited by examiner

*Primary Examiner* — Vincent Q Nguyen
(74) *Attorney, Agent, or Firm* — Vidas, Arrett & Steinkraus, P.A.

(57) ABSTRACT

Method and apparatus for the measurement of mass or density and/or for the measurement of the humidity in a plurality of portioned units in a non-metallic carrier material, which provides the following: a microwave measuring instrument, consisting of at least one microwave resonator for generating at least one resonance mode in a spatially limited measurement area and an analyzing unit for analyzing at least one variable of the at least one resonance mode, a conveying device for the carrier material, which transports the carrier material with the portioned units through the measurement area, the microwave measuring instrument measures at least one variable of the at least one resonance mode at a time when only the carrier material without portioned unit is in the measurement area, and at a time when the portioned unit is at least partially in the measurement area, the analyzing unit subtracts the variable measured for the carrier material from the measurement values for the portioned unit, and determines a value of the humidity and/or of the mass or density of the portioned unit from at least one difference by way of an input-output map.

12 Claims, 5 Drawing Sheets

APPARATUS AND METHOD FOR THE MEASUREMENT OF MASS AND DENSITY AND/OR FOR THE MEASUREMENT OF THE HUMIDITY OF PORTIONED UNITS

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention is related to a method and an apparatus for the measurement of mass or density and/or for the measurement of the humidity in a plurality of portioned units in a carrier material.

From EP 0 889 321, the entire contents is incorporated herein by reference, a microwave resonator is known which is realised as a cavity resonator in order to measure a profile of density and/or humidity on a sample in the longitudinal direction of the sample. The known microwave resonator has a cylindrical cavity, through which the sample to be measured is moved and whose changes of the resonance with respect to the empty condition permit unambiguous conclusions regarding the values of the humidity and density profiles of the sample.

From EP 1 316 630, the entire contents is incorporated herein by reference, an apparatus and a method is known for acquiring the mass and the humidity content of fibrous material in a preparatory machine for spinning works. In this, the material to be measured is guided through a cavity resonator, and the changes of the resonance properties of the microwave resonator that occur with respect to the empty condition of the resonator are recorded. Further, the speed of the material that runs through is measured.

From EP 1 467 191 B1, the entire contents is incorporated herein by reference, a method and an apparatus is known to determine the mass of portioned units of active agents, like for instance capsules, tablets and dragées. In order to sort out capsules whose mass is not within a given tolerance range at the exit of a machine for filling the capsules, it is envisioned to transport the capsules within an air flow through the microwave resonator. By way of corresponding switches or air pulses, sorting the capsules according to different masses or humidities into different containers is performed, wherein the microwave resonator measurement unit is either integrated into the machine itself, together with the throw-out mechanism, or is positioned next to the machine as an independent unit.

The present invention is based on the objective to provide a method and an apparatus for the measurement of mass or density and/or for the measurement of the humidity in a plurality of portioned units in a non-metallic carrier material which reliably measures the portioned unit independently from its carrier material by way of simple means.

BRIEF SUMMARY OF THE INVENTION

In the method of the present invention, a measurement of the mass or density and/or a measurement of the humidity is performed in a plurality of portioned units in a non-metallic carrier material, which might also be formed inhomogeneously. The method uses a microwave measuring instrument, which consists of at least one microwave resonator for generating at least one resonance mode in a spatial measurement area, and of an analysing unit for analysing at least one variable of each resonance mode. Further, the method of the present invention includes a conveying device for the carrier material, which transports the carrier material with the portioned units through the measurement area of the at least one microwave resonator. According to the present invention, the microwave measuring instrument measures the at least one variable of the at least one resonance mode at a time when only the carrier material without portioned unit is in the measurement area, and in addition at a time when the portioned unit is at least partially in the measurement area. In this, a total of at least two variables is measured at a time, that is to say, in the case of one resonance mode, two variables are measured for the same, in the case of plural resonance modes, one or plural variables can be acquired in at least one resonance mode. The analysing unit subtracts the variable measured for the carrier material from the corresponding measurement values that are measured when the portioned unit is at least partially in the spatial measurement area. This subtraction penults not only the detection of the properties of the portioned unit, but yields also a measurement signal which is independent from temperature-caused changes of the shape, from soiling- or wear phenomena on the resonator. In this way, measurements of empty resonance conditions can be omitted that are normally necessary in order to detect such disturbance parameters. By way of an input-output map, the analysing unit determines a value for the humidity and/or mass or density of the portioned unit from the differences. Depending on the geometrical dimensions of the portioned units, the density of the portioned unit can be measured in the method of the present invention by way of the input-output map too, provided that the geometrical dimensions of the portioned units do not change. The input-output map for a measurement variable like mass, density of humidity indicates the value of the measurement variable, depending on at least two differences that had been determined by the analysing unit.

The method of the present invention is based on the finding that the resonance effects of the portioned units are independently superimposed to those of the carrier material, and therefore can be measured conjointly and be separated into their individual components again. In order to computationally eliminate the effect of the carrier material from the measurement result, whose properties might be inhomogeneous, a subtraction is carried out in the method of the present invention. The method of the present invention measures the local properties of the carrier material only then when only the carrier material is in the measurement area. In case that the portioned unit is at least partially also within the measurement area, the changes in the resonance characteristics of the resonance mode detected by the microwave measuring instrument are corrected for the changes of the resonance characteristics that were acquired for the carrier material only. In the method of the present invention, it has come out that the properties of the portioned unit can be acquired very reliably in this way, and at the same time fluctuations in the carrier material, temperature changes and other influences which occur during the execution of the method can be compensated reliably. A decisive requirement for this is that the microwave measurement area must be formed such that the carrier material itself can always be measured between two portioned units that are embedded into the carrier web, without influence of the portioned units. Thus, the pure carrier material measurement forms a reference variable which makes the empty resonance measurement dispensable, whose execution is mostly accompanied by some expense. Changes of the empty resonance need not to be detected in the method of the present invention.

In a preferred embodiment of the method of the present invention, the portioned units are disposed permanently within the carrier material. The portioned units are transported through the measurement area with the aid of the carrier material. Thus, in the method of the present invention an additional conveyor belt or a rotating disc for supplying the portioned units to the measurement area is omitted. Instead, the transportation of the portioned units takes place conjointly with the carrier material, wherein the portioned units remain in the carrier material permanently, and can be separated from the carrier material only by destroying the same.

In a preferred further development of the method of the present invention, it is envisioned that in case that the extension of the portioned units in the transportation direction is smaller than the extension of the measurement area in the transportation direction, the extremal value in time of the measurement values for the portioned unit is analysed. For the analysis, those measurement values are analysed which had occurred during the transportation of the portioned unit through the measurement area. Thus, by the extremal value consideration, those measurement values at which the portioned units are only partially in the measurement area, or not in the sensitive part of the measurement area, are not taken into account, instead only that condition of the portioned units is acquired in which the entire sample is in the spatially homogeneous measurement area region of the at least one microwave resonator.

A further preferred embodiment is related to the case that the extension of the portioned unit in the transportation direction is greater than or equal to the extension of the measurement area in the transportation direction. In this case, the situation occurs that the portioned unit enters the measurement area and occupies the same completely for a certain duration, and subsequently exits from the measurement area again. For such a case, the measurement values recorded by the analysing unit are averaged in order to determine the difference for the input-output map for mass and humidity. If a spatial resolution of the humidity- and/or density distribution within the portioned unit is not relevant in the present method, that value can be subtracted from the mean value or the summed up value which had been measured for the carrier material. However, if a spatially resolved distribution of humidity and mass or density, respectively, is of interest in the longitudinal direction of the portion unit having extension, the value characterising the carrier material has to be subtracted from each individual measurement value.

In order that the analysing unit can decide whether the carrier material is in the measurement area conjointly with the portioned unit, the analysing unit can be given notice by the conveying device that a portion is at least partially in the spatial measurement area, by separate sensors like light barriers for instance.

Preferably, the carrier material is supplied to the measurement area continuously. A particular advantage of the method of the present invention is that even carrier material containing the portioned units can be supplied to the measurement area continuously, so that the method of the present invention can be executed in co-operation with a packaging or filling machine.

A preferred embodiment of the method of the present invention is used in the production of tea bags. In this embodiment, a web of sheathing material made of filter paper with portioned tea bags therein is supplied as a carrier material to the microwave measurement instrument. Then, the method of the present invention acquires the humidity and/or the mass of the tea that is contained in the tea bags when the measurement signal between two tea chambers is acquired as that of the carrier material.

Also, the method of the present invention can be used when a web of sheathing material is used as the carrier material. Portioned tobacco bags can be supplied to the microwave measuring instrument in the web of sheathing material. Such tobacco bags are also designated as snus bags. The humidity and/or the mass of the snus powder contained in the bag is acquired by the method of the present invention.

In a further possible embodiment, even a continuous cigarette filter strand constructed as a multi-filter can be supplied to the microwave measurement instrument as a carrier material. This strand includes also spatially limited sections in which portions of activated charcoal e.g. are contained, which are either embedded in the filter material or portioned in the quasi endless cigarette filter strand in chambers ("cavities" or "sleeves"). In this case, the reference measurement of the carrier material must be made at defined filter material sections or at certain filter web sections which do not contain any particular active or ingredient substances.

Thus, not only the mass proportion of the portioned units of the individual filter segments in difference to that of the carrier material can be determined (for instance the mass of the activated charcoal or of other additives to the filter material), but also the correct order of the individual segments can be monitored by means of the measurement values that are typical for each region, as well as the position of the transitions between the segments. In this case, the extension of the measurement field in the movement direction of the strand has to be as small as possible, in order to achieve the necessary spatial resolution.

In a further embodiment, the cigarette filter strand can be doped with capsules. Such capsules in the cigarette filter strand are then measured by the microwave resonator with respect to whether they feature a desired mass which is within a tolerance range. Also, by analysing the humidity value it may be determined if the capsule incorporated into the filter strand is intact. In this case, the position for the carrier material reference measurement is given by such filter strand pieces between two capsules at which the respective neighbouring capsules are both situated outside the measurement field.

In a preferred further development of the method of the present invention, the analysing unit can analyse the mass of the capsules measured in the cigarette filter rod conjointly with the point of time at which the capsules had been in the measurement area. By doing so, it can be determined whether the measured capsules having the desired mass do have a predetermined distance within the cigarette filter rod. When doping a cigarette filter strand with capsules, this information is important in addition, because the cigarette filter strand is later cut into single filters.

The apparatus of the present invention serves for the measurement of mass or density and/or for the measurement of the humidity in a plurality of portioned units in a non-metallic carrier material. The apparatus has a microwave measuring instrument, a conveying device, a measurement device and an analysing unit. The microwave measuring instrument consists of at least one microwave resonator for generating at least one resonance mode in a spatially limited measurement area. The analysing unit analyses at least one variable of the at least one resonance mode. In doing so, when it is worked with only one resonance mode, at least two variables of this single resonance mode are analysed, whereas in an embodiment with plural resonance modes, one or plural variables can be selected for each one of the resonance modes. The conveying device transports the non-metallic carrier material with the portioned units through the measurement area of the at least one microwave resonator.

Each measurement device that is provided according to the present invention measures at least one variable of the at least one resonance mode at a time when only the carrier material without portioned unit is in the measurement area, and at a time when the portioned unit is at least partially in the measurement area. The device has subtraction means and an input-output memory. The subtraction means subtracts the variable measured for the carrier material from the measurement values for the portioned unit. The input-output memory has a predetermined input-output map, which indicates a value for humidity and/or mass or density of the portioned unit for a difference generated by the subtraction.

In the apparatus of the present invention, the properties of the portioned unit can be acquired reliably, wherein fluctuations in the density of the carrier material, temperature changes and other influences which may occur in the measurement are compensated at the same time.

In a preferred embodiment, in case that the extension of the portioned unit in the transportation direction is greater than or equal to the extension of the measurement area in the transportation direction, an average of the measurement values of the portioned units is determined, or the sum of the measurement values which had been measured during the transportation of the portioned unit through the measurement area is analysed. In this case, the analysing unit makes sure that the portioned unit is measured over the entire length.

In a preferred embodiment, a conveying means is provided, which indicates to the analysing unit that there is only carrier material in the measurement area. Through this, the measurement values that were recorded for the carrier material only can be reliably discriminated from the measurement values for the portioned unit.

In a further embodiment of the apparatus of the present invention, a cloth web of portioned tea bags is provided as the carrier material. In an alternative embodiment, a web of sheathing material with portioned tobacco bags, snus tobacco bags in particular, is provided as the carrier material. Alternatively, a filter strand with filters can also be provided as a carrier material, wherein the cigarette strand may feature in particular multi-filters having individual regions with activated charcoal. A cigarette filter strand with capsules can also be provided as a carrier material, for instance with menthol capsules. When measuring a cigarette filter strand that is doped with capsules, the analysing unit can analyse the mass of the capsules contained in the cigarette filter strand together with their position, in order to determine if the capsules having the desired mass do have a predetermined distance, and/or a predetermined position in the cigarette filter strand.

DETAILED DESCRIPTION OF THE FIGURES OF THE DRAWINGS

DETAILED DESCRIPTION OF THE INVENTION

Figure 1:
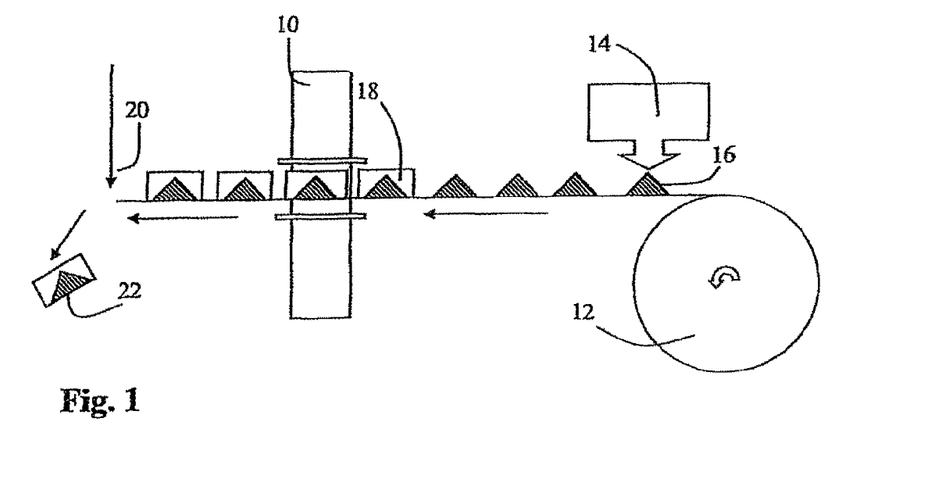
FIG. 1 shows the measurement of portioned units in packaging machines and a microwave arrangement for mass- and humidity measurement.

While this invention may be embodied in many different forms, there are described in detail herein a specific preferred embodiment of the invention. This description is an exemplification of the principles of the invention and is not intended to limit the invention to the particular embodiment illustrated FIG. 1 shows in a schematic representation a microwave resonator 10 which is arranged within a production machine with quasi endless portioned webs of sheathing material as a carrier web. Starting from a sheathing material reservoir 12, the web of sheathing material is rolled off and provided with the corresponding portioned units 16 of a material via a portioning device 14. Tobacco, tea or other materials may be in question for this. In step 18, the portioned units present on the web of sheathing material are fixed by sealing the web of sheathing material. Thus, different methods known in the state of the art can be used. The closed portions are then guided through the measurement area of the microwave resonator 10. In a subsequent step 20, individual portioned units 22 whose mass or humidity is not within a predetermined tolerance range can be sorted out. Thus, the carrier web material is a part of the produced product. Whereas its properties might change, for the evaluation of the product's quality is of interest only the mass (or density respectively) and/or the humidity of the portions that are embedded into the carrier web.

The microwave resonator 10 serves to generate a stationary standing microwave field, through which the measured product together with the carrier web is moved through. For this purpose, a microwave resonator when realised as a cavity generator has a passage opening which is frequently cladded with non-metallic material for sample guiding.

At least two measurement variables are necessary in the measurement, wherein with one microwave resonator, at least one measurement variable is obtained for each resonance mode which changes permanently with the material that is present in the field. One of the measurement variables is the actual resonance frequency. This measurement variable depends on the shape of the resonator, on the mass and the chemical composition, on the humidity of the product in the measurement field in particular. When determining the mass, it is advantageous to measure the resonance frequency at a resonance mode in which the electric measurement field of the stationary wave is constant in the direction that is transversal to the movement direction of the sample. This is the case in a basic mode of the resonance for instance, which has always a maximum of the field in the resonator axis, which spatially changes only slightly in the direction transversal to the movement.

When the portioned units are moved through the microwave resonator, there results the resonance frequency f(V), which is measured in the region of the carrier material with the portioned unit, and the resonance frequency f(Ref), which is measured as a resonance frequency between the portioned units on the carrier material. In the method of the present invention, the evaluation for the portion takes place by the following measurement variable (the absolute value of the difference being used, because the resonance frequency with portion is normally smaller than that without portion):

$$A(\text{Port}) = Abs[f(V) - f(\text{Ref})].$$

Figure 2:
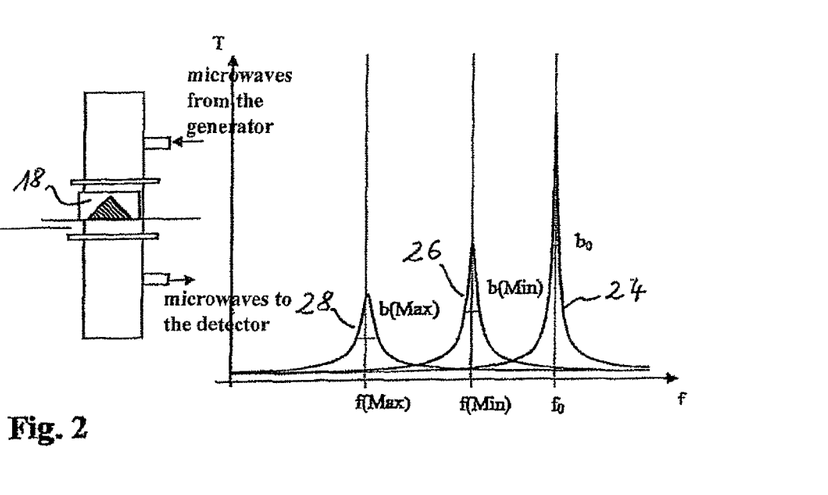
FIG. 2 shows the measurement signals A and B in a frequency representation when using a microwave resonator in the product maximum and between two product maxima, when only the carrier material is in the measurement field. In this holds A=Abs[f(Max)−f(Min)] and B=b(Max)−b(Min), wherein f signifies the resonance frequency and b the resonance width at half the amplitude and the designations Max and Min indicate the maximum or respectively the minimum of the values.

A second measurement variable of the microwave measuring instrument is designated by B. In principle, for the second measurement variable there is the possibility to represent the width of the same resonance curve as an expression of the attenuation of the microwave through the resonator itself, like that through the carrier material and the embedded portion. This approach to determine the variable B is explained in more detail in the context of FIG. 2. For the sake of illustration, FIG. 2 shows the course of the resonance curve 24 in the empty condition of the microwave resonator with the frequency f0 and the width b0, which are not taken into account in the entire measurement, however. Further, two resonance curves are drawn in by way of example, which differ from the above, wherein the resonance curves 26 and 28 have smaller resonance frequencies than the resonance curve in the empty condition. The resonance curve 26 having the width b(Min) characterises the condition in which only the carrier material is in the measurement field of the resonator, whereas the resonance curve 28 having the width b(Max) describes the condition in which both carrier material and portioned unit are in the measurement field. For the analysis of the example shown in FIG. 2, in which the packaged portion 18 is completely in the interior of the microwave resonator, the maximum width of the resonance curve 28 can be taken for the analysis.

Generally holds: When the portioned units are moved through the microwave measuring instrument, there results that resonance width b(V) which is measured in the region of the carrier material with the portioned unit, and the resonance width b(Ref), which is measured between the portioned units on the carrier material. In the method of the present invention, the analysis for the portion takes place by the variable:

$$B(\text{Port}) = b(V) - b(\text{Ref}).$$

Figure 3:
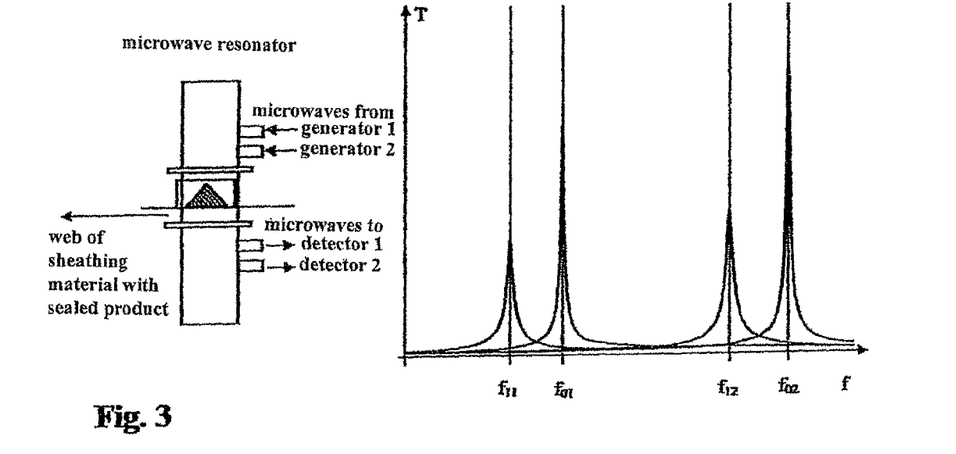
FIG. 3 shows the measurement signals A and B in a frequency representation when using a microwave resonator and two sufficiently spaced apart resonance modes, wherein at each mode, the position of the resonance frequency f1 with a portion in the measurement field, and without portion in the measurement field f0 (with carrier material only) is shown. In this holds A=Abs[f11−f01] and B=Abs[f12−f02], wherein f01 is the first resonance frequency and f02 the second resonance frequency without portion, and f11 the first resonance frequency and f12 the second resonance frequency with portion in the measurement field.
Figure 4:
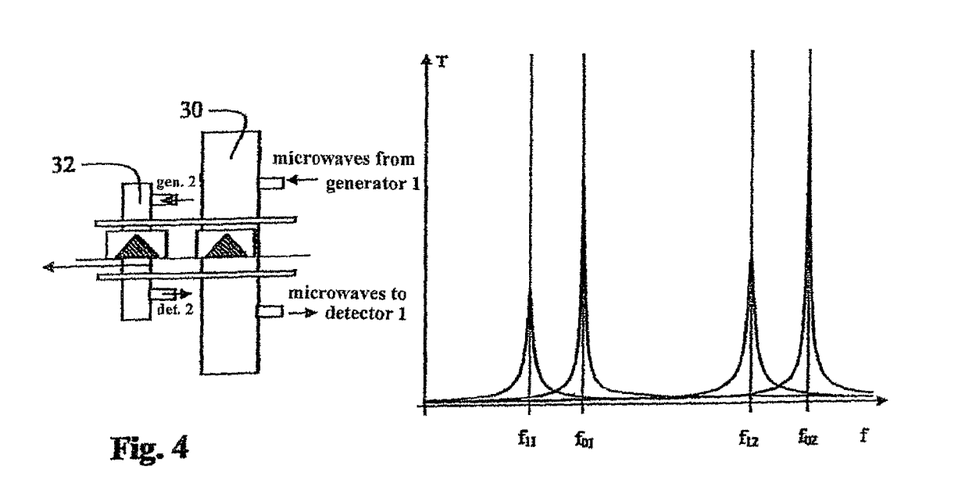
FIG. 4 shows the measurement signals A and B in a frequency representation when using two microwave resonators arranged one behind the other in the basic mode, whose resonance frequencies are sufficiently spaced apart. In this, at each resonator f1 designates the position of the resonance frequency with a portion in the measurement field, and f0 that without portion in the measurement field (with carrier web only). As the carrier web with the portioned units moves through the two resonators subsequently, the corresponding measurement values in the resonator 2 are obtained with a delay. Taking into account this shift, there results A=Abs [f11−f01] and B=Abs[f12−f02].

Two alternative possibilities to determine the second measurement variable B(Port) are represented in the context of FIGS. 3 and 4. FIG. 3 shows an example wherein the detuning of another resonance mode with portioned unit with respect to the resonance with carrier material only is acquired as the second measurement variable B(Port). At a resonance frequency that is excited with respect to the basic mode and which is at a sufficient distance from the resonance of the basic mode, for instance of at least for 0.5 GHz, better 3-4 GHz, the shifts of the resonance frequency represented in FIG. 3 do occur. For the first resonance frequency, in the condition in which only the carrier material is in the measurement field, there results the resonance frequency f01, which is shifted to the second resonance frequency f11 by the input of the portioned unit that is embedded into the carrier material. For the second resonance fed in by the microwave resonator, a resonance frequency f02 results in the condition with carrier material only, and in the condition of the microwave resonator carrier material plus portioned unit a resonance frequency f12. The above method uses the frequency dependence of the dielectric constant, and therefore it needs resonance frequencies which have a distance as great as possible. In this kind of analysis, no attenuation effects of the material that result in the widening of the resonance are therefore analysed at all. This can impart great advantages always then when the attenuation measurement yields no unambiguous measurement effects for an accurate measurement of humidity and mass, for instance when the attenuation-based calibration curve runs too flat above the humidity axis. Then, the transition to the measurement method without attenuation measurement is helpful in most cases:

$$A(\text{Port}) = Abs[f11 - f01]$$

$$B(\text{Port}) = Abs[f12 - f02].$$

The detuning B recorded in this way serves to compensate for the humidity dependence of the recorded measurement value A.

In the variant shown in FIG. 4, a first resonator 30 and a second resonator 32 are used. Both resonators are operated in the basic mode of cylindrical cavities at frequencies sufficiently spaced apart from each other—for instance at least for 0.5 GHz, better 3-4 GHz. Even with these two microwave resonators, again the shifts of the resonance frequencies can be analysed, but of two different resonators operated in the basic mode, however.

Through this, one has the possibility for the measurement to use basic modes having a relatively constant measurement field in the direction transverse to the movement of the portions, which would otherwise occur only once when using one resonator only, at far distant frequencies—which leads to an increase of the measurement accuracy in particular in the humidity measurement of inhomogeneous samples, and via the humidity compensation also in the mass measurement. In this, at each resonator f1 indicates the position of the resonance frequency with portioned unit in the measurement field, and f0 the resonance frequency with carrier web only in the measurement field. As the carrier web with the portioned units moves consecutively through the two resonators, the corresponding measurement values in the resonator 2 are obtained with a delay. Taking this shift into account, these two independent measurement variables result (the absolute value of the difference being used again, because the resonance frequency with portion is normally smaller than that without portion):

$$A(\text{Port}) = Abs[f11 - f01]$$

$$B(\text{Port}) = Abs[f12 - f02].$$

In principle, the variables A(Port) and B(Port) acquired in FIGS. 1 to 4 by different methods and defining the properties of portioned units contained in a carrier material, are proportional to the mass of the portioned units, but depend in different ways from the chemical composition, namely the humidity and the alcohol content, at products with small, polar molecules in particular. In some cases, the rigid mass proportionality can only be achieved by adding a small offset constant. Then, when forming the quotient of B(Port) and A(Port), a value independent from the mass results for the chemical composition of the material of the portions, in particular for the humidity of the portioned units indicated in mass percent. This mass-independent quotient can be calibrated against a reference method and be memorised as a calibration relation for the humidity of the portions, for example in a characteristic curve.

Moreover, the measurement with the two parameters A(Port) and B(Port) of the portioned units offers also the possibility to indicate the mass (or, at constant sample geometry, the density) of the product independently from fluctuations in the chemical composition, the humidity in particular, by calibrating the measurement signals B(Port) and A(Port) as linear combinations against the reference mass (or density) of the portion. The coefficients of this linear combination can then be memorised as parameters of the calibration relation for the mass or density of the respective portion material, in a characteristic curve for instance.

Figure 5:
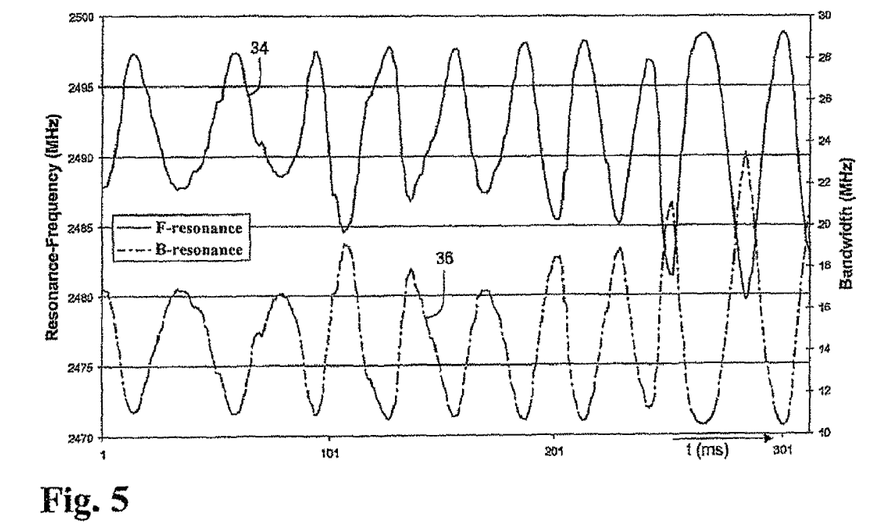
FIG. 5 shows the course in time of the microwave measurement values of a resonator in the process of the movement of a chain of snus portions in a web of sheathing material through a microwave resonator.

The course in time of the measurement variables for the resonance frequency and the line width of a resonance mode recorded in this way is shown by way of example in FIG. 5, when a carrier material consisting of pulp with tobacco powder portions moves through the measurement field of a microwave resonator. One recognises clearly in FIG. 5 that the course of both values, plotted against the time t, has a periodical structure. In fact, the amplitude values vary, and smaller superimposed fluctuations in the measurement values themselves. However, the course of both measurement variables plotted against time has the same period, which is caused by the movement of the portioned units that are periodically arranged in the measurement field. The measurement values at which the resonance frequency has a maximum and the width has a minimum can be regarded as reference variables for the pure carrier material, the empty resonator and possible resonator soiling. On the other hand, the minima of the resonance frequency and the maxima of the half-width are caused by the portioned units plus the carrier material. The difference of overall and reference signal yields then the measurement variables A(Port) and B(Port) that are characteristic for the portioned units.

These measurement variables A(Port) and B(Port) are independent of soiling, wear of the resonator, temperature changes or other property changes in the resonator. Because of the mass proportionality of the two variables A(Port) and B(Port), an increase and a decrease of the two measurement signals is observed during the movement of a portion of a product. This can be recognised by the maxima and minima that occur for the case of the moved portioned units 18 from FIG. 1 in FIG. 5.

Figure 6:
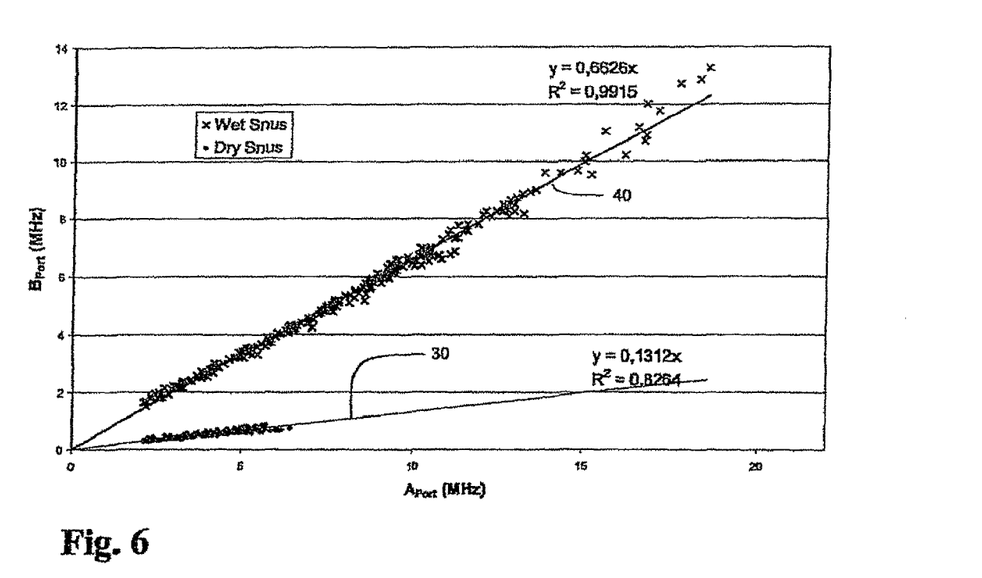
FIG. 6 shows the recorded measurement values for two groups of snus portions having different humidities, wherein the B-values are plotted against the corresponding A-values.

FIG. 6 shows the measurement values of tobacco portions from FIG. 1 in the form of a plot of B(Port)—against A(Port)—measurement values when the portioned units 18 move through the microwave measuring instrument 10, two samples with strongly different humidity having been used in the measurement. In the example shown in FIG. 6, the regression lines 38 and 40 leading through the zero point due to the mass proportionality of A(Port) and B(Port) are drawn in, whose slope is a measure for the humidity of the portioned units and can be analysed by a characteristic calibration line. In case that the extension of the portioned units is smaller than the measurement field, it is sufficient in the analysis of the signals according to FIG. 5 to use the maximum, values for the values of A and B. However, when the extension of the sample is greater than the measurement field of the resonator in the movement direction, forming the average value between two neighbouring reference measurement positions is advantageous for characterising the portioned units. In order to determine the reference variables for the carrier material without portioned units, the maximum or the minimum of the curves 34 and 36 may be used, for instance. Alternatively, it is also conceivable that the analysing unit has a separate control signal which indicates if there is a portion or only the carrier material in the measurement area just now.

Up to 20.000 measurement values of A and B per second can be recorded by the microwave measuring instrument in the practical use. When a portion moves through the sensor with a velocity of 10 m/s, up to 20 values for A(Port) and B(Port) can be determined for the portion to be measured when the measurement field extension and the sample dimension are each 1 cm. This is about the upper limit for the velocity or the lower limit for the sample dimension, respectively, up to which it can be worked in the microwave region with the measurement techniques that are technically at hand today. At realistic, usual production speed of 1 m/sec, the number of measurement values per sample centimetre is already increased to 200, by which also samples can be measured that are significantly smaller than 1 cm.

If one relates A and B always to the reference measurement, the presence of a portioned unit is always characterised in that a maximum is exceeded, at A as well as at B.

When the dimension of the measured portion is smaller than the homogeneous field region of the microwave resonator extending in the transportation region, the entire sample is in the carrier material when the maximum signal for A is reached. In this case, the maximum of the measurement variable A can be used, as was already mentioned. The behaviour in time is analogous for B.

When the measurement area is not at all or only insufficiently homogeneous in the axis direction, the dimension of the measured sample exceeds the extension of the homogeneous field region which serves as the measurement area. In this case it has proven to be substantially more accurate to use the average value over the course of A(Port) and B(Port) instead of the maximum value. The average value can be generated between two minima, for instance.

Figure 7:
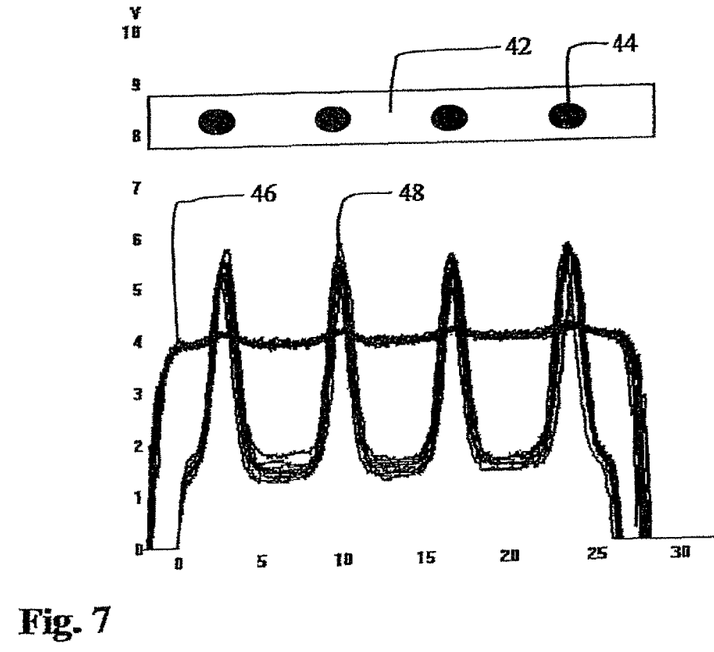
FIG. 7 shows the measurement values in a spatial representation at a high speed detection for the position of menthol capsules embedded into filter strand material.

FIG. 7 shows the utilisation of the method of the present invention with a filter rod 42, into which capsules 44 filled with menthol are incorporated, wherein a single resonance method that analyses the resonance frequency and the width of the resonance curve is used. The B-values generated over the length of the filter rod 42 are essentially constant in this, as long as the capsules 44 in the filter rod 44 are intact. The also shown A-values have a maximum at the corresponding positions of the capsules 44. When the capsules are not intact however, even the B-values show a local maximum. By analysing the A and B values it is possible to check in the filter rod whether the capsules in the filter rod 42 are intact and complete and situated at the correct position of the filter rod.

In FIG. 7, the plotted measurement values are directly converted into a position of the capsules in millimetres. In order to answer the question whether the capsules 44 are positioned in the desired distance to each other in the filter strand 42, the distance between the maxima 48 can be analysed, for instance.

Figure 8:
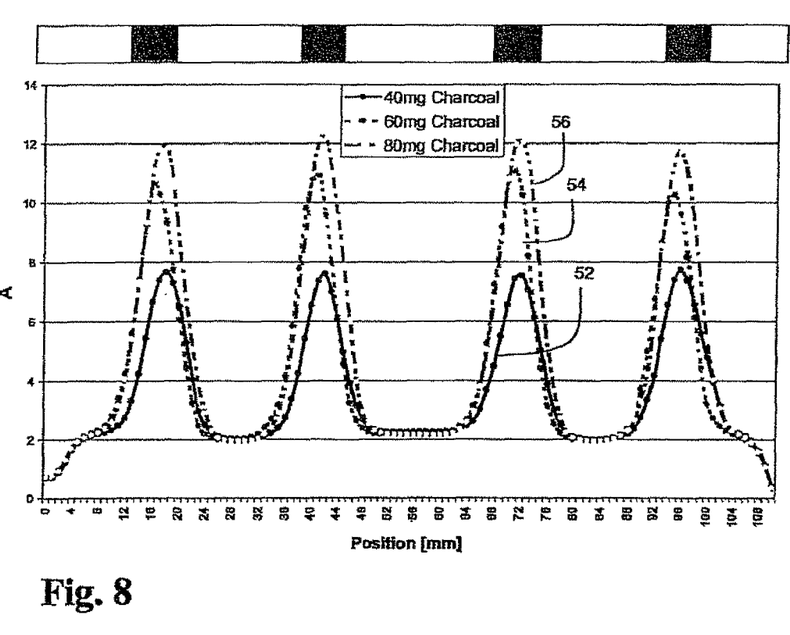
FIG. 8 shows the measurement values in a spatial representation at a high speed detection of the mass and the position of activated charcoal chambers in filter rods, embedded into a paper web sleeve and filter rod material.

FIG. 8 discusses the method of the present invention for instance when it is applied to a quasi endless filter strand on a multi-filter rod machine. The values 52 show the filter strand with a filled multi-filter, 40 mg activated charcoal being in the filter chamber. The course of curve 54 shows a somewhat more filled filter chamber which contains 60 mg of activated charcoal. Curve 56 shows the course of the resonance frequencies in a filter strand with about 70 mg of activated charcoal per chamber. The difference between the resonance frequencies with portion plus carrier material and the frequencies at the reference sites yields A(Port), which is an ideal measure for the activated charcoal content in each single chamber.

Figure 9:
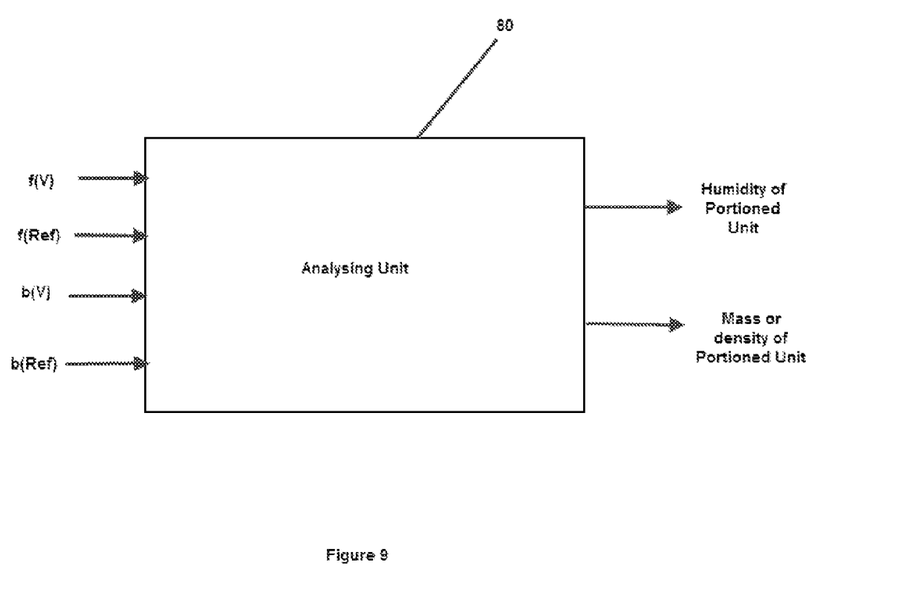
FIG. 9 is a block diagram showing the inputs to the analyzing unit, and its outputs.

FIG. 9 shows a block diagram of the analyzing unit 80, which receives inputs f(V), f(Ref),b(V), and b(Ref), and determines the outputs, which are the humidity of the proportioned unit and/or the mass or density of the proportioned unit.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method for the measurement of mass or density and/or for the measurement of the humidity in a plurality of portioned units in a non-metallic carrier material, comprising the steps of:
   generating at least one resonance mode in a spatially limited measurement area;
   analysing at least one variable of the at least one resonance mode;
   transporting the carrier material with the portioned units through the measurement area;
   measuring the at least one variable of the at least one resonance mode at a time when only the carrier material without portioned unit is in the measurement area, and at a time when the portioned unit is at least partially in the measurement area;
   subtracting the measured variable for the carrier material from the measurement values for the portioned unit;
   determining a value of the humidity and/or of the mass or density of the portioned unit from at least one difference by way of an input-output map, and
   characterised in that in case that the extension of the portioned units in the transportation direction is smaller than the extension of the spatial measurement area in the transportation direction, the analysing unit analyses the extremal one of the measurement values for the portioned unit which had occurred during the transportation of the portioned unit through the measurement area.

2. The method according to claim 1, characterised in that the measurement values for the carrier material are established when a maximum in the resonance frequency and a minimum of the line width occurs.

3. The method according to claim 1, characterised in that a web of sheathing material made of filter paper with portioned tea bags is supplied as a carrier material to the microwave measurement instrument.

4. The method according to claim 1, characterised in that a web of sheathing material with portioned tobacco bags, snus tobacco bags in particular, is supplied as a carrier material to the microwave measurement instrument.

5. The method according to claim 1, characterised in that a cigarette filter strand with multi-filters is supplied as a carrier material to the at least one microwave measurement instrument.

6. The method according to claim 5, characterised in that the cigarette strand with multi-filters has individual regions with activated charcoal.

7. A method for the measurement of mass or density and/or for the measurement of the humidity in a plurality of portioned units in a non-metallic carrier material, comprising the steps of:
   generating at least one resonance mode in a spatially limited measurement area;
   analysing at least one variable of the at least one resonance mode;
   transporting the carrier material with the portioned units through the measurement area;
   measuring the at least one variable of the at least one resonance mode at a time when only the carrier material without portioned unit is in the measurement area, and at a time when the portioned unit is at least partially in the measurement area;
   subtracting the measured variable for the carrier material from the measurement values for the portioned unit;
   determining a value of the humidity and/or of the mass or density of the portioned unit from at least one difference by way of an input-output map, and
   characterised in that in case that the extension of the portioned unit in the transportation direction is greater than or equal to the extension of the spatial measurement area in the transportation direction, the analysing unit analyses an average value or the sum of the measurement values for the portioned unit which had occurred during the transportation of the portioned unit through the measurement area.

8. A method for the measurement of mass or density and/or for the measurement of the humidity in a plurality of portioned units in a non-metallic carrier material, comprising the steps of:

generating at least one resonance mode in a spatially limited measurement area;

analysing at least one variable of the at least one resonance mode;

transporting the carrier material with the portioned units through the measurement area;

measuring the at least one variable of the at least one resonance mode at a time when only the carrier material without portioned unit is in the measurement area, and at a time when the portioned unit is at least partially in the measurement area;

subtracting the measured variable for the carrier material from the measurement values for the portioned unit;

determining a value of the humidity and/or of the mass or density of the portioned unit from at least one difference by way of an input-output map, characterised in that a cigarette filter strand that is doped with capsules is supplied as a carrier material to the microwave measurement instrument, and further characterised in that the analysing unit analyses the mass of the capsules measured in the cigarette filter rod together with the point of time at which the capsules were in the measurement area, with respect to whether the capsules having the desired mass do have a predetermined distance, and/or a predetermined position in the cigarette filter rod.

9. An apparatus for the measurement of mass or density and/or for the measurement of the humidity in a plurality of portioned units in a non-metallic carrier material, which features the following: a microwave measuring instrument, consisting of at least one microwave resonator for generating at least one resonance mode in a spatially limited measurement area and an analysing unit for analysing at least one variable of the at least one resonance mode, a conveying device for the carrier material, which transports the carrier material with the portioned units through the measurement area, a measurement device that measures at least one variable of the at least one resonance mode at a time when only the carrier material without portioned unit is in the measurement area, and at a time when the portioned unit is at least partially in the measurement area, the analysing unit features subtraction means which subtract the variable measured for the carrier material from the measurement values for the portioned unit, and an input-output memory in which a predetermined input-output map is stored which indicates a value of the humidity and/or of the mass or density of the portioned unit for a difference generated by the subtraction means, characterised in that in case that the extension of the portioned unit in the transportation direction is greater than or equal to the extension of the spatial measurement area in the transportation direction, the analysing unit analyses an average or the sum of the measurement values for the portioned unit which had occurred during the transportation of the portioned unit through the measurement area.

10. The apparatus according to claim 9, characterised in that the conveying device indicates to the analysing unit when there is only carrier material in the measurement area.

11. The apparatus according to claim 9, characterised in that a web of sheathing material with portioned tobacco bags, snus tobacco bags in particular, is provided as a carrier material.

12. An apparatus for the measurement of mass or density and/or for the measurement of the humidity in a plurality of portioned units in a non-metallic carrier material, which features the following: a microwave measuring instrument, consisting of at least one microwave resonator for generating at least one resonance mode in a spatially limited measurement area and an analysing unit for analysing at least one variable of the at least one resonance mode, a conveying device for the carrier material, which transports the carrier material with the portioned units through the measurement area, a measurement device that measures at least one variable of the at least one resonance mode at a time when only the carrier material without portioned unit is in the measurement area, and at a time when the portioned unit is at least partially in the measurement area, the analysing unit features subtraction means which subtract the variable measured for the carrier material from the measurement values for the portioned unit, and an input-output memory in which a predetermined input-output map is stored which indicates a value of the humidity and/or of the mass or density of the portioned unit for a difference generated by the subtraction means, characterised in that a cigarette filter strand that is doped with capsules is provided as a carrier material, and further characterised in that the analysing unit analyses the mass of the capsules measured in the cigarette filter strand together with the point of time at which the capsules were in the measurement area, with respect to whether the capsules having the desired mass do have a predetermined distance, and/or a predetermined position in the cigarette filter strand.

* * * * *